United States Patent [19]

Rzewinski

[11] Patent Number: 4,494,932
[45] Date of Patent: Jan. 22, 1985

[54] DENTAL CLEANING APPARATUS AND METHOD

[75] Inventor: Leonard Rzewinski, New Hyde Park, N.Y.

[73] Assignee: Cooper LaserSonics, Inc., Santa Clara, Calif.

[21] Appl. No.: 467,916

[22] Filed: Feb. 18, 1983

[51] Int. Cl.³ .............................................. A61C 3/02
[52] U.S. Cl. ...................................... 433/88; 51/426; 51/436
[58] Field of Search ......................... 433/88, 125, 216; 51/426, 427, 428, 436, 437, 438, 439; 222/630, 173; 118/308

[56] References Cited

U.S. PATENT DOCUMENTS

| | | | |
|---|---|---|---|
| 727,030 | 5/1903 | Tilghman | 51/437 |
| 2,292,897 | 8/1942 | Nielsen | 51/436 |
| 2,324,425 | 7/1943 | Rasmussen | 51/436 |
| 2,759,266 | 8/1956 | Cassani | 51/438 |
| 2,899,106 | 8/1959 | Weinert | 222/83.5 |
| 3,815,286 | 6/1974 | Piet | 51/427 |
| 3,852,918 | 12/1974 | Black | 51/436 |
| 3,882,638 | 5/1975 | Black | 51/428 |
| 3,972,123 | 8/1976 | Black | 433/88 |
| 4,067,150 | 1/1978 | Merrigan | 222/196 |
| 4,174,571 | 11/1979 | Gallant | 51/428 |
| 4,214,871 | 7/1980 | Arnold | 433/88 |

FOREIGN PATENT DOCUMENTS 654428 12/1937 Fed. Rep. of Germany ........ 51/437

Primary Examiner—John J. Wilson
Attorney, Agent, or Firm—Vorys, Sater, Seymour & Pease

[57] ABSTRACT

An improved apparatus for dispensing cleaning powder in an air stream to be directed onto the surface of teeth includes a fluid-tight chamber for containing a supply of cleaning powder and having an open space above the powder, with an elongated tube mounted in the chamber and having a bottom end adjacent the bottom of the chamber and an open top end above the powder supply in the chamber, and with openings in the tube permitting limited flow of powder into the tube by gravity. Air under pressure is directed into the bottom of the tube to entrain the powder and discharge it in an air-powder stream from the open top of the tube. An outlet in the sidewall of the chamber permits air and powder to flow out under pressure, and a movable deflection member deflects the stream of air and entrained powder from the open top of the tube above the powder supply and generally toward the outlet.

25 Claims, 5 Drawing Figures

DENTAL CLEANING APPARATUS AND METHOD

BACKGROUND OF THE INVENTION

1. Field of the Invention

This invention relates to apparatus for cleaning teeth, and more particularly to an improved apparatus for use in the removal of tenaceous stain and heavy plaque from exposed tooth surfaces by simultaneously directing a stream of air containing entrained cleaning powder and a stream of water onto the tooth surfaces to be cleaned.

2. Description of the Prior Art

While an effective home care program including regular brushing and flossing is considered essential to dental hygiene, such home care normally cannot be completely effective in removing stain and plaque, particularly from relatively inaccessible surfaces between the teeth and from pits and fissures. Accordingly, it is normally recommended that a dental care program include regular, periodic professional cleaning. Such professional cleaning operation conventionally has involved the removal of calculus, particularly from subgingival surfaces, and the cleaning of the exposed enamel surfaces for the removal of stain and plaque. Cleaning the enamel surface normally has involved polishing with an abrasive material, typically pumice, in a paste by use of a rotary rubber cup. This method is effective in cleaning accessible surfaces, but cannot remove all stains from deep pits and fissures, even after protracted use of the pumice and rubber cup.

It has also been known, for example from U.S. Pat. Nos. 3,882,638 and 3,972,123, to employ air-abrasive equipment for cleaning of teeth, using insoluble abrasive particles entrained in an air stream directed onto the tooth surface while simultaneously discharging a water stream in surrounding relation to the air-abrasive stream. The use of soluble abrasive particles or pellets, and of powdered abrasive material, respectively, are also known from U.S. Pat. Nos. 4,214,871 and 4,174,571.

The prior art abrasive cleaning devices which have been most widely used commercially employ water delivered in one or more streams surrounding the air-abrasive stream to form a converging water curtain to provide a wet surface for more effective cleaning, eliminate dust from within the patient's mouth and to dissolve and flush the abrasive material and carry it away for removal by the conventional suction equipment. Although the use of insoluble abrasive material has not met with widespread commercial acceptance, soluble abrasives, particularly a sodium bicarbonate cleaning powder, has been widely accepted and is very effective in cleaning stain and plaque from deep pits and fissures or other surface areas which could not be effectively reached by the rotating rubber brush and pumice technique. However, the reliable feeding of the cleaning powder at a uniform, accurately controllable rate has not always been possible with the prior art devices. For example, U.S. Pat. No. 4,214,871 discloses the use of an aspirator effect to create suction sufficient to lift the soluble abrasive particles from a supply container attached to the apparatus, but discloses no means for metering, or controlling, the rate of flow of the abrasive particles.

U.S. Pat. No. 3,882,638, mentioned above, discloses a cleaning powder supply chamber and dispensing mechanism of a type which has been used on commercial dental cleansing apparatus. This system includes a powder receptacle or chamber including a removable top closure member with an elongated tube projecting through the closure terminating in a closed end positioned adjacent the bottom of the chamber. A concentric sleeve mounted on the closure member projects downwardly in surrounding relation to the tube, the air under pressure admitted to the annular space between the tube and sleeve is discharged through outlets in a spacer member at the bottom of the sleeve. The air pressurizes the chamber and escapes through inlet ports in the bottom portion of the tube, with the escaping air blowing powder from the container into the tube for delivery to an airline connected to the handpiece. Although a bleed-off valve is provided for the abrasive chamber, this valve is closed during operation and all air flowing into the chamber must pass through the ports in the bottom of the tube.

In another prior art dental cleaning apparatus of this general type, manufactured by the assignee of the present invention, a secondary air outlet is provided in the top closure of the powder chamber. The third outlet vents the air space above the body of powder directly to the main air supply line leading to the handpiece. In use of this device, more air can be discharged into the mass of cleaning powder adjacent the bottom of the chamber than passed upward through the central tube to deliver cleaning powder to the handpiece. This excess air passes upward through and fluffs the cleaning powder before escaping through the secondary air outlet. Again, however, air flowing through the body of powder and into the ports in the bottom of the tube was relied on as the primary source of cleaning powder delivered to the handpiece. Variations in air pressure were relied upon to control the abrasive powder flow rate.

SUMMARY OF THE INVENTION

It is a primary object of the present invention to provide an improved air abrasive dental cleaning apparatus of the type employing a soluble abrasive powder material entrained in and delivered by a stream of air onto the surface to be cleaned while simultaneously discharging a water curtain around the air-abrasive stream.

Another object is to provide such an apparatus which includes an improved cleaning powder supply and dispensing mechanism.

Another object is to provide such an apparatus in which the powder supply chamber and dispensing mechanism includes means for accurately and easily adjusting the rate of flow of cleaning powder from the apparatus without requiring adjustment of air pressure.

Another object is to provide such an apparatus including an improved cleaning powder chamber and dispensing apparatus which does not rely upon the flow of pressure air through the body of powder in the chamber to forceably eject powder through ports in a central delivery tube mounted within the chamber.

In the attainment of the foregoing and other objects and advantages of the invention, an important feature resides in providing a central tube projecting upwardly from the bottom of the abrasive powder chamber and terminating in an opening within the upper portion of the chamber, with openings in the bottom portion of the tube to permit the flow of abrasive powder into the tube by gravity. Air, under pressure, is discharged into the bottom of the tube, at a point below the openings, to entrain the abrasive powder and discharge the powder from the top of the tube. An outlet in a wall of the chamber adjacent the top provides an escape for the air and entrained abrasive powder discharged from the open top of the tube, and adjustable means are provided for deflecting the air-abrasive stream relative to the outlet opening to increase or decrease the amount of abrasive powder contained in the air escaping from the outlet for delivery to the dental cleaning handpiece.

The bottom portion of the powder chamber is contoured to facilitate gravity feed of the supply of powder toward the bottom of the chamber to provide a continuous flow of powder through the openings in the bottom of the central tube. The flow of pressure air through the tube past the openings has an erosive effect tending to assure a continuous flow of powder into the tube. This erosive effect may also result in a small proportion of the air discharged into the tube escaping through the openings to aerate, or fluff the abrasive powder in the bottom of the chamber and further assure a substantially uniform continuous flow of abrasive into the tube. Also, if desired, means may be provided for discharging a small volume of air directly into the bottom portion of the chamber in outwardly spaced relation to the central tube to assist in fluffing the abrasive powder to assure a continuous, uniform flow of powder. When fluffing air is admitted, means are provided for limiting the volume of such air to avoid force feeding or "blowing" excessive powder through the openings into the central delivery tube.

BRIEF DESCRIPTION OF THE DRAWINGS

Other features and advantages of the invention will become apparent from the detailed description contained hereinbelow, taken in conjunction with the drawings in which.

DETAILED DESCRIPTION OF THE PREFERRED EMBODIMENTS

Figure 1:
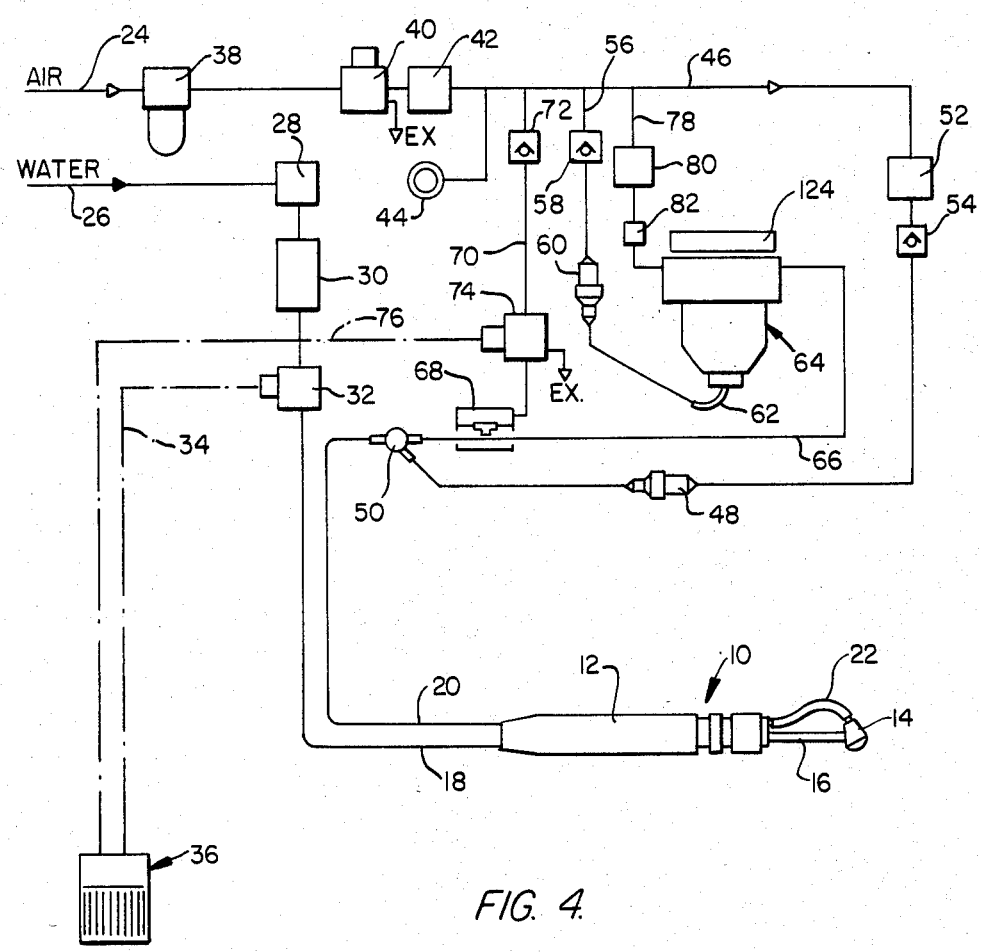
FIG. 1 is a schematic view of a dental cleaning apparatus embodying the present invention.

Referring now to the drawings in detail, a handpiece used in directing an air-abrasive stream and surrounding water spray curtain onto the tooth surface is designated generally by the reference numberal 10 and includes an elongated handle portion 12 and a nozzle head 14 supported on a rigid water supply tube 16. A flexible water supply conduit 18 extends into the handle 12 and is connected to the rigid tube 16 within the handpiece for supplying water under pressure to the head 14. A second flexible supply conduit 20 also extends into the handle 12 and is connected to a removable, flexible tube 22 for supplying air under pressure and cleaning powder to the cleaning head 14. Air is supplied to the apparatus through an air supply line 24 from a suitable compressed air source such as a conventional dental office air supply compressor, not shown, and water is supplied through a separate line at 26 from a suitable source such as a municipal water supply line. A water pressure regulator 28 is in line 26 to maintain the water pressure at a constant desired level, and a suitable heater 30 connected in the water supply line maintains the water to the handpiece at a desired temperature which will be comfortable to a patient. Flow of warm water to the handpiece is controlled by a solenoid actuated valve 32 connected, through line 34, to a three-position foot actuated control switch 36. The water supply system and the structure of the handpiece, per se, may be of a conventional construction and as such form no part of the present invention other than being necessary to the overall operation of the dental cleaning apparatus.

Referring still to the schematic of FIG. 1, air under pressure flowing through line 24 passes initially through an inlet, or preliminary filter 38 which removes water, contaminants, dust particles and the like, then through a main solenoid actuated shut-off valve 40 and pressure reducer-regulator 42 which maintains the air pressure to the apparatus at a constant, desired level. A suitable gauge 44 may be provided downstream of regulator 42 to provide a continuous visible display of system air pressure. Valve 40 is vented to atmosphere to bleed pressure from the system, through line 46, when the valve is closed. From pressure regulating valve 42, air flows through line 46 and a variable flow restrictor, preferably a manually operated needle valve 52 to one-way check valve 54 to prevent reverse flow through needle valve 52. Air flows through a one-way filter 48 to a "Y" fitting 50 connected to the flexible air conduit 20 to supply air to the handpiece 10.

Air also flows from line 46 through line 56 to the coupling member 62 mounted on the bottom of a powder chamber assembly designated generally as 64. A one-way check valve 58 and an air filter 60 are connected in line 56. From chamber 64 air flows through a line 66 to the Y-fitting 50 to deliver entrained cleaning powder particles to the flexible conduit 20 to flow with air from line 46 through handpiece 10 and flexible tube 22 to be discharged from the cleaning head 14. Flow of air and cleaning powder particles through line 66 is controlled by a normally closed air energized diaphragm actuated pinch valve 68. Actuating air is supplied to valve 68 through a line 70 connected to line 46 and a one-way check valve 72 connected in line 70 prevents reverse flow through this line. Flow through line 70 to valve 68 is controlled by a normally closed, energized open solenoid valve 74 connected, through line 76, to the foot actuated control switch 36. When valve 74 is energized, pinch valve 68 is vented to atmosphere to permit the pinch valve to open and air to flow through line 66.

When pinch valve 68 is energized to close line 66, cleaning powder chamber 64 will normally remain pressurized through line 56 and through a second conduit 78 connected between line 46 and an inlet in the top portion of chamber 64. A flow restrictor 80 connected in line 78 limits the rate of flow through this line as pointed out hereinbelow, and an air filter 82 connected in the line serves both to filter air flowing into chamber 64 and to prevent cleaning powder particles from escaping into the system when the system is vented to atmosphere by closing main flow control valve 40. With valve 40 closed and the system vented to atmosphere through this valve, chamber 64 can be opened for cleaning and servicing or for refilling with cleaning powder as soon as gauge 44 indicates system pressure has reached zero.

With valve 40 open normal bleed air flows through line 46 and tube 20 to be discharged from handpiece 10.

With valve 40 open and control switch 36 actuated to its first detent position, water flow control valve 32 is energized open to permit flow of irrigation or rinsing water through handpiece 10. When the foot actuated control 36 is moved to its second detent or fully depressed position, water control valve 32 will remain open, and valve 74 will be energized and pressure air will open pinch valve 68 to permit a flow of particulate cleaning powder and air from chamber 64 and line 66 through the handpiece 10.

Figure 2:
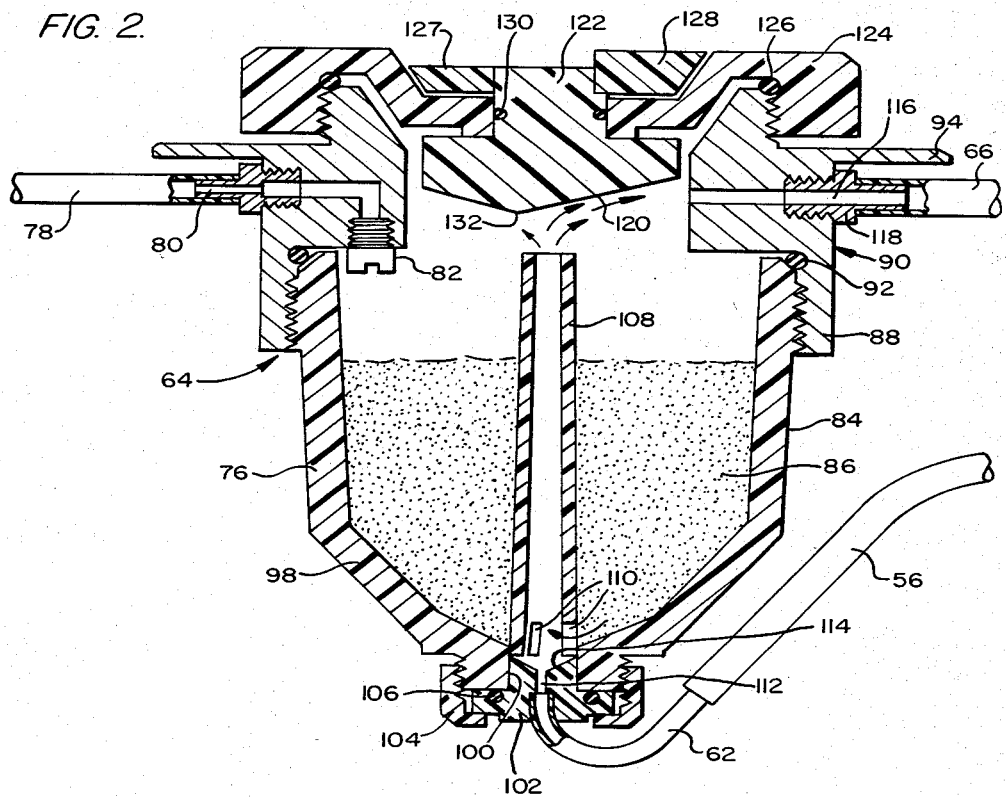
FIG. 2 is an enlarged sectional view of the abrasive powder supply and dispensing mechanism according to the present invention.

Referring now to FIG. 2, a preferred embodiment of the cleaning powder chamber and dispensing mechanism according to this invention is shown as including a powder hopper or bowl 84 for retaining a supply of soluble abrasive cleaning powder indicated generally at 86. Powder bowl 84 is preferably molded from a high-strength transparent synthetic resin material to permit viewing of the contents. The bowl has an open top and is supported by male threads adjacent its open top which cooperate with female threads on a downwardly extending skirt 88 of a rigid support housing 90. An O-ring seal 92 provides a fluid-tight seal between support housing 90 and the top peripheral portion of bowl 84. A radially extending flange 94 on housing 90 is adapted to mount the assembly on a support plate or panel member of a suitable cabinet structure for the dental cleaning apparatus. Suitable fasteners, not shown, may be used to secure the flange to the support panel.

Bowl 84 includes a generally cylindrical or slightly tapered body portion 96 extending from its open top throughout a major portion of its height, and bottom portion 98 which is tapered inwardly at an angle which will promote gravity feed of the powder mass 86 toward the bottom central portion of the bowl. A bore 100 is formed in and extends through the bottom wall portion of powder bowl 84, and an air nozzle structure 102 mounted on the bottom of the bowl by threaded nut 104 projects into the bore 100. A resilient O-ring seal 106 provides a fluid-tight seal between the bottom end surface of bowl 84 and the air nozzle 102.

An elongated powder supply tube 108 extends axially through powder bowl 84 and has its open bottom end in fluid communication with the bore 100. Tube 108 may be separately formed and secured in position within the bowl by screw threads, adhesive bonding or other means, but preferably is integrally molded with bowl 84 as shown in FIG. 2. A plurality of longitudinally extending, radially spaced powder dispensing openings 110 are formed in and extend through the wall of tube 108 at its bottom end to permit a limited, metered flow of cleaning powder into the bottom portion of the tube.

Air nozzle 102 has a small diameter axial bore 112 extending therethrough, with a counterbore formed in its downwardly directed end receiving the end of rigid tube coupling member 62. Tube 62 is permanently secured, as by welding or silver soldering, to the body of the air nozzle 102 to provide a secure coupling means for tube 56 to supply air, under pressure, through the air nozzle to be discharged into the bottom open end of the central tube 108. Preferably the upwardly directed face of nozzle 102 is flared at a relatively wide cone angle as shown at 114 to promote expansion of air discharged through the bore 112 and to produce turbulence in the air as it enters the bottom of the tube. Air flowing into the bottom of tube 108 entrains the particles of abrasive powder and carries them upward through the center of the bowl to be discharged in an upwardly directed stream from the open top end of the tube. Expansion of air and the resulting turbulence in the vicinity of the openings 110 produces an erosion effect on the body of powder to assist in the gravity dispensing of powder through the openings to maintain a constant, highly uniform concentration of powder particles in the stream of air flowing upwardly through tube 108.

Air and entrained powder particles discharged from tube 108 escape from the top region of the powder chamber and dispensing assembly 64 through a radially extending outlet 116 in housing 90. Tube 66 is connected in communication with the outlet 116 by a threaded fitting 118 to deliver the air-abrasive stream to the handpiece as described above. The air and entrained powder particles are discharged from the top of tube 108 in a substantially vertical stream which is directed against an inclined surface 120 on the particle flow control member 122 which redirects the powder particles in a generally horizontal direction. Flow control member 122 is rotatably mounted in a central opening of a cap or closure member 124 threadably mounted on the open top of housing 90. An O-ring seal 126 provides a fluid-tight seal between closure 124 and housing 90. A retaining flange 127 having a position indicator or pointer 128 is mounted on the upwardly projecting end of flow control member 122, and an O-ring seal 130 provides a fluid-tight seal between the central opening in closure 124 and the flow control member 122. Flow control member 122 is of transparent material providing a viewing or sight window for observing powder feeding against cone deflection surface 120.

The downwardly directed inclined surface 120 is preferably generally conical, with the apex 132 of the cone being eccentric with respect to the common vertical, or longitudinal axes of the contral opening in closure 124 and tube 108. When the flow control member 122 is rotated so as to position apex 132 in substantially radial alignment with and spaced at its maximum distance from outlet opening 116, powder particles discharged from tube 108 will tend to strike a portion of surface 120 which is inclined toward the entrance of outlet 116. This position results in the maximum concentration of abrasive powder particles being entrained in the air flowing through the outlet and tube 66 to the handpiece 10. At the same time, a substantial portion of the powder particles discharged from tube 108 will not enter outlet 116 and will settle back into the mass of powder in the bowl 84. The conical deflection surface 120 tends to produce a generally fan-shaped stream of air and powder with the maximum concentration of powder particles in the portion of the stream radially aligned with the apex 132 regardless of the relative position of the member 122. This enables easy adjustment of the concentration of the powder in the air stream discharged from the handpiece by simply rotating the flow control member 122 from the maximum delivery position in which the pointer 128 is aligned with the outlet 116 toward the minimum delivery position in which indicator 128 points 180° from outlet 116 and apex 132 is at its closest approach to the outlet 116. Even in the minimum delivery position, some powder particles will be entrained in the air escaping through outlet 116. An infinite variation is available between these two extreme positions.

Air admitted into the top portion of the chamber from line 78 through flow restrictor 80 and filter 82 mixes with the powder particle laden air in the top portion of the powder dispenser and escapes through outlet 116. Thus, the air flow volume in tube 66 is greater than that admitted through tube 56 into the bottom of the powder chamber. This reduced, or controlled air flow volume upward through the central tube 108 also enables better control of powder particle flow through openings 110 while utilizing the erosion effect of the turbulent air on the body of powder through the openings to facilitate a more uniform flow of powder into the base of the tube.

As indicated above, the bottom section 98 of powder bowl 84 is tapered downwardly and inwardly at an angle to assure gravity feed of the powder toward the bottom center of the chamber. It has been found that a cone angle "a" of about 75° will produce this desired gravity feed when the preferred sodium bicarbonate cleaning powder is used. This cone angle may extend throughout the bottom from wall 96 to the outer periphery of tube 108 or alternatively the cone angle may be increased in the area adjacent the tube as shown in FIG. 2. For example, in a configuration which has been constructed and successfully tested, the maximum diameter of the inner surface of the inclined bottom wall was 1.74 inches, and the bottom wall inclined inwardly at an included angle of 75° to a diameter of 1.0 inch and at an included cone angle of 120° from that point to the outer periphery of the central tube. This configuration resulted in reliable, constant feed of the powder material without requiring agitation or the injection of fluffing air into the powder mass in the powder bowl.

Figure 4:
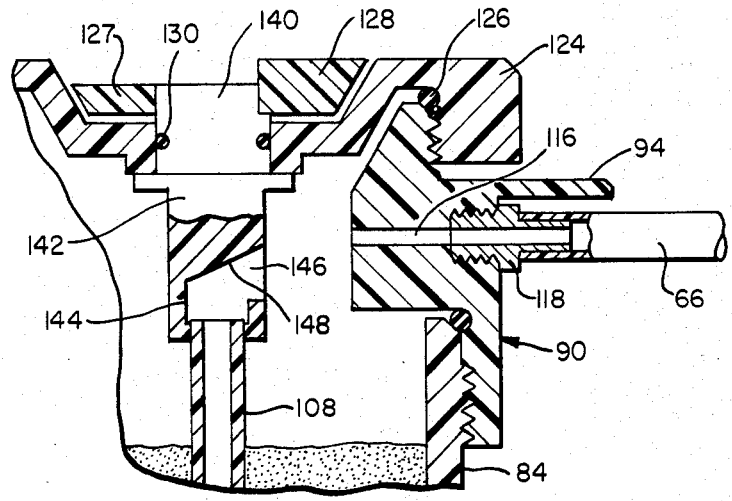
FIG. 4 is a fragmentary sectional view similar to FIG. 2 and showing an alternate embodiment of the invention.

Referring now to FIG. 4, and alternate embodiment of the invention employing a slightly different means for controlling the discharge rate of the abrasive powder material from the chamber is illustrated. Since the remainder of the dispensing apparatus is substantially identical to that just described, only the portion of the structure necessary to show the changes is illustrated in FIG. 4, and common reference numerals are employed to designate common parts employed in the two embodiments. In this alternate embodiment, a flow control member 140 is mounted in the central opening in top cover 124 and retained by the retaining flange 127. Control member 140 includes a downwardly projecting substantially cylindrical body portion 142 having a cylindrical bore 144 formed in its bottom end adapted to telescopically receive the upwardly projecting top end of central tube 108. Bore 144 terminates at its upper end in an inclined surface 146, and a notch-shaped opening 148 formed in one side of the cylindrical member communicates with the bore 144 to provide an exit for air and entrained powder particles flowing upwardly through tube 108. Thus, such particles will strike the inclined surface 146 and be deflected laterally in the manner described in FIG. 2. Inclined surface 146 may be substantially planar or curved to produce the desired powder particle concentration pattern in the deflected air-powder stream. For example, a downwardly concave surface may be provided to produce a more concentrated stream of powder particles, or a downwardly convex surface may be employed to produce a wider dispersion of the powder particles. In this embodiment, the cylindrical body 142 is substantially coaxial with the tube 108, and the pointer 128 may be employed to manually rotate the control member to vary the concentration of powder particles relative to the outlet 116 as described above.

Figure 5:
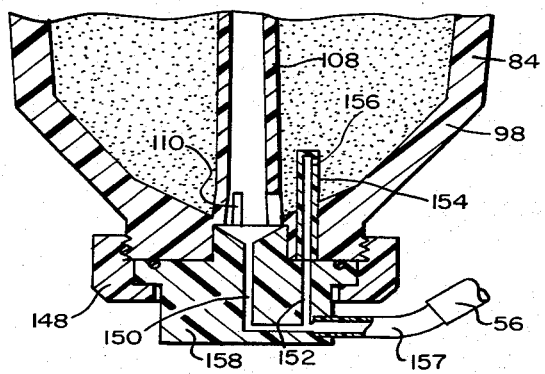
FIG. 5 is a fragmentary sectional view showing a further embodiment of the invention.
Figure 3:
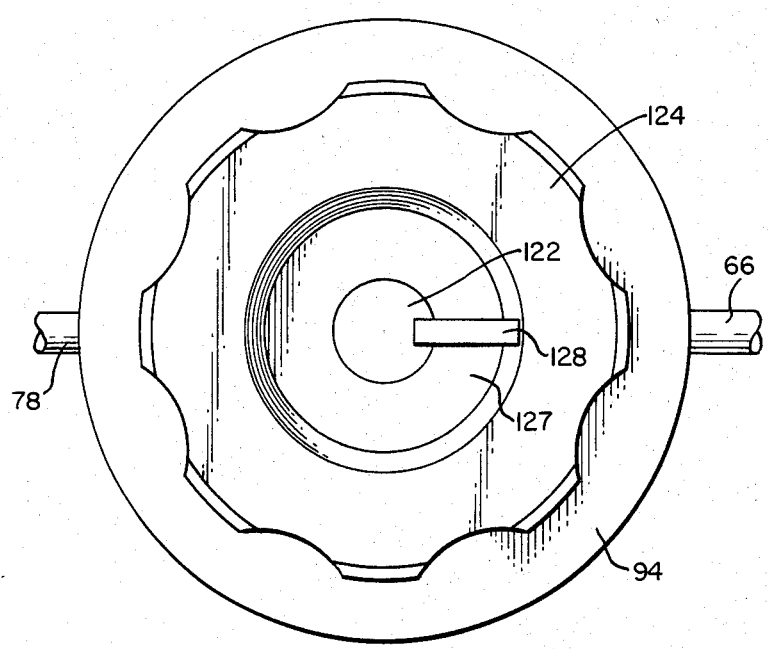
FIG. 3 is a top plan view of the apparatus shown in FIG. 2.

Although the powder dispensing mechanisms described above with regard to FIGS. 2 and 4 have been found to produce highly uniform particle flow at an easily controllable rate, it is conceivable that some abrasive powder material might be less fluent than the sodium bicarbonate cleaning powder presently preferred as the soluble abrasive material. In the embodiment of FIG. 5, a slight modification of the apparatus is shown wherein the low volume of air is admitted into the powder mass adjacent the bottom of the bowl 84 in outwardly and upwardly spaced relation to the metering holes 110 to provide slight agitation or fluffing action of the cleansing powder. Again, in FIG. 5, only that portion of the apparatus is shown necessary to illustrate the modification, it being understood that the remainder of the structure may be substantially identical with that described above with regard either to FIG. 2 or FIG. 4. Thus, in this embodiment, air from the tube 56 is discharged into the coupling member 157 rigidly mounted, as by welding or silver soldering, to an inlet nozzle member 158 retained on the bottom of the powder bowl 84 by a threaded nut 148 substantially as described above. An axial bore 150 discharges air into the bottom of tube 108 and a second air passage 152 is formed in nozzle member 146 in radially spaced relation to the axial bore 150. A flow restricting tubular member 154 is rigidly mounted in and extends through the bottom portion of the powder bowl 84 and has its bottom end in fluid communication with the air passage 152.

Tubular member 154 includes outlet means for admitting a limited quantity of air to be discharged in outwardly spaced relation to the tube 108 through a small outlet opening 156 to produce slight agitation or fluffing of the powder in the area outboard of and preferably above the openings 110. While a single outlet 156 is illustrated, it should be understood that various means may be provided for controlling the flow of air from tube 154; for example, a porous sintered metal plug may be employed in the end of the tube to permit air to flow outwardly through the plug while preventing powder from passing into the tube 154.

It should be apparent that various modifications could readily be made to the apparatus. For example, it is contemplated that the central tube 108 might be made from a resilient material, with means adjustable from the exterior of the powder dispenser assembly being provided for deflecting the open top of the tube relative to a fixed or movable deflection surface to vary the concentration of particulate cleaning powder in the air stream flowing from the apparatus. Thus, while preferred embodiments of the invention have been disclosed and described, it should be apparent that the invention is not so limited and it is intended to include all embodiments which would be apparent to one skilled in the art and which come within the spirit and scope of the invention.

What is claimed is:

1. In a system for cleaning teeth in which a stream of air having cleaning powder particles entrained therein and a separate stream of water are directed against the tooth surface to be cleaned, an improved cleaning powder dispensing apparatus for providing a controlled flow of cleaning powder particles comprising, a powder chamber for containing a supply of cleaning powder to be dispensed, the powder chamber having sidewalls, a bottom wall and top closure means and having a maximum powder supply level spaced below said top closure means, an elongated tube mounted in said chamber and having a bottom end adjacent said bottom wall and an open top end spaced above said maximum powder supply level, powder dispensing opening means providing a gravity flow path for powder from the bottom portion of said chamber into the bottom end portion of said elongated tube, first air inlet means for directing a flow of air under pressure upwardly through said elongated tube from a point below said powder dispensing opening means for conveying powder from the bottom portion of said elongated tube and discharging the powder from the open top end of the tube, an outlet opening in the sidewall of the chamber at a point above said maximum powder supply level, deflection means positioned to engage and deflect at least a portion of the air and powder particles discharged from said open top of said elongated tube in a direction toward the sidewall of the chamber whereby air admitted into the bottom of said elongated tube and powder particles conveyed through the tube escape through said outlet opening, conduit means for conveying the escaping air and powder particles from said outlet opening in a stream for direction onto the tooth surface to be cleaned.

2. The system defined in claim 1 wherein said air inlet means comprises means defining an air passage extending through said bottom wall and communicating directly with the bottom end portion of said elongated tube.

3. The system defined in claim 2 wherein the diameter of said air passage is substantially smaller than the diameter of said elongated tube whereby the velocity of air is substantially reduced upon passage from said air inlet means into said elongated tube.

4. The system defined in claim 3 wherein said powder dispensing opening comprises a plurality of openings extending through the wall of said elongated tube adjacent said bottom wall of said chamber.

5. The system defined in claim 4 wherein said powder dispensing openings are in the form of elongated generally longitudinally extending slots formed in the wall of said elongated tube.

6. The system defined in claim 1 wherein said deflection means comprises baffle means defining a deflection surface inclined with respect to the longitudinal axis of said elongated tube, and means for moving said baffle means for varying the direction of deflection of the air and powder particles discharged from the open top end of the elongated tube.

7. The system defined in claim 1 further comprising second air inlet means for admitting a controlled flow of air into said chamber at a position above said maximum powder supply level.

8. The system defined in claim 1 wherein said powder chamber comprises an open topped bowl formed from a transparent material and having downwardly extending sidewalls and an inwardly inclined bottom wall, said bottom wall being inclined at an angle which will assure gravity flow of dental cleaning powder along its surface, and wherein said top closure means includes means for engaging and supporting said bowl and cooperating therewith to define an enclosed space above the maximum powder supply level.

9. The system defined in claim 8 wherein said top closure means includes a support housing adapted to engage and support said bowl adjacent its open top, said housing extending upwardly from said bowl and having an open top, and a removable closure member adapted to be mounted on and sealingly close said open top of the support housing.

10. The system defined in claim 9 wherein said deflection means comprises baffle means defining a deflection surface inclined with respect to the longitudinal axis of said elongated tube, and support means mounting said deflection means on said housing, said support means including actuating means extending through and accessible outside said housing means for manual rotation of said baffle means about an axis substantially parallel to the longitudinal axis of said elongated tube.

11. The system defined in claim 10 further comprising second air inlet means for admitting a controlled flow of air into said chamber at a position above said maximum powder supply level.

12. The system defined in claim 10 further comprising means for admitting a controlled flow of air into the bottom portion of said chamber at a location spaced outwardly from said elongated tube and above said powder dispensing opening means to fluff powder in the bottom portion of said bowl and thereby assure a continuous substantially uniform gravity flow of powder into said elongated tube.

13. The system defined in claim 1 wherein said deflection means comprises a deflection member mounted in vertically spaced relation to the open end of said elongated tube, means rotating said deflection member about the longitudinal axis of said elongated tube, and actuating means accessible outside of said powder chamber for rotating said deflection member, said deflection member having the downwardly directed surface inclined with respect to the longitudinal axis of said elongated tube.

14. The system defined in claim 13 wherein said deflection surface is a substantially conical surface, the apex of said conical surface being laterally spaced from the axis of rotation of said deflection member whereby rotation of the deflection member produces a continuously varying deflection surface engaged by air and entrained dental cleaning powder discharged from the open end of the elongated tube.

15. Apparatus for dispensing dental cleaning powder at a controlled, variable rate in a substantially uniform continuous stream comprising, in combination, a fluid-tight chamber for containing a supply of dental cleaning powder to be dispensed, said chamber including a powder supply container having an open top, downwardly extending side walls and a bottom wall, and means providing a fluid-tight closure on the open top of the container and defining an open space above the top of the container, an elongated tube mounted within the container and having a bottom end adjacent said bottom wall and an open top end communicating with the open space above the top of said container, powder inlet means in said elongated tube adapted to permit dental cleaning powder in said container to flow by gravity into said tube at a rate greater than the dental cleaning powder is dispensed from the apparatus, first air inlet means for directing a stream of air under pressure upwardly through said elongated tube from a point below said powder inlet means to entrain and convey the dental cleaning powder through said elongated tube to be discharged from the open top end of said elongated tube, outlet means located above the open top of said container to permit air and dental powder to escape from the chamber, and baffle means adapted to engage and to deflect said stream of air and entrained dental cleaning powder discharged from the open top of said elongated tube in the general direction of said outlet means whereby a portion only of the dental cleaning powder entrained in the air stream discharged from said elongated tube will be dispensed through said outlet means and the remainder will fall by gravity back into said container.

16. The apparatus defined in claim 15 further comprising support means mounting said baffle means for movement in said fluid-tight chamber, and activating means operable to move said baffle means to vary the direction of deflection of said stream of air and entrained dental cleaning powder relative to said outlet to thereby vary the concentration of dental cleaning powder in the air escaping through said outlet means.

17. The apparatus defined in claim 16 further comprising second air inlet means for admitting a controlled flow of air under pressure into said fluid-tight chamber in the open space above said container.

18. A method of dispensing dental cleaning powder in an air stream for use in cleaning teeth comprising, directing a stream of air under pressure upwardly through an elongated tube having one end located below the top of a mass of dental cleaning powder contained in a fluid-tight chamber with the other end of the elongated tube being open and positioned above the mass of powder in the chamber, permitting dental cleaning powder to flow by gravity into the elongated tube whereby the dental cleaning powder is entrained in the stream of air and discharged from the open top end of the elongated tube, the rate of flow of dental cleaning powder into the elongated tube being greater than the maximum desired dispensing rate, permitting air and suspended dental cleaning powder particles to escape from the fluid-tight chamber through an outlet opening located in a side wall of the chamber above the mass of dental cleaning powder, deflecting the stream of air and entrained dental cleaning powder issuing from the open top of the elongated tube toward the side wall of the container and in the general direction of the outlet opening, and varying the direction of deflection of the stream of air and entrained dental cleaning powder relative to the outlet opening to thereby control the concentration of dental cleaning powder in the air escaping from the outlet opening.

19. The method defined in claim 18 wherein the step of deflecting the stream of air and entrained dental cleaning powder comprises directing the stream issuing from the open top of the elongated tube onto a deflecting surface inclined relative to the longitudinal axis of the elongated tube, and rotating the deflecting surface about an axis generally parallel to the longitudinal axis of the elongated tube to thereby vary the direction of deflection of the stream of air and entrained dental cleaning powder.

20. The method defined in claim 19 further comprising the step of admitting a controlled flow of air into the fluid-tight chamber at a point above the level of the mass of dental cleaning powder in the chamber and permitting the air admitted above the cental cleaning powder to flow from the chamber through the outlet opening.

21. In a system for cleaning teeth in which a stream of air having cleaning powder particles entrained therein and a separate stream of water are directed against a tooth surface to be cleaned, an improved cleaning powder dispensing apparatus for providing a controlled flow of cleaning powder particles comprising:

a powder chamber for containing a supply of cleaning powder to be dispensed, the powder chamber having sidewalls, a bottom wall and top closure means and having a maximum powder supply level spaced below said top closure means, an elongated tube mounted in said chamber and having a bottom end adjacent said bottom wall and an open top end spaced above said maximum powder supply level, powder dispensing opening means providing a gravity flow path for powder from the bottom portion of said chamber into the bottom end portion of said elongated tube, first air inlet means for directing a flow of air under pressure upwardly through said elongated tube from a point below said powder dispensing opening means for conveying powder from the bottom portion of said elongated tube and discharging the powder from the open top end of the tube, an outlet opening in the sidewall of the chamber at a point above said maximum powder supply level, adjustable deflection means positioned to engage and deflect at least a portion of the air and powder particles discharged from said open top of said elongated tube in a direction toward the sidewall of the chamber whereby air admitted into the bottom of said elongated tube and powder particles conveyed through the tube escape through said outlet opening, and conduit means for conveying the escaping air and powder particles from said outlet opening in a stream for direction onto the tooth surface to be cleaned.

22. The system defined in claim 21 wherein said air inlet means comprises means defining an air passage extending through said bottom wall and communicating directly with the bottom end portion of said elongated tube.

23. The system defined in claim 21 wherein the diameter of said air passage is substantially smaller than the diameter of said elongated tube whereby the velocity of air is substantially reduced upon passage from said air inlet means into said elongated tube.

24. The system defined in claim 21 wherein said powder dispensing opening comprises a plurality of openings extending through the wall of said elongated tube adjacent said bottom wall of said chamber.

25. The system defined in claim 21 wherein said powder dispensing openings are in the form of elongated generally longitudinally extending slots formed in the wall of said elongated tube.

* * * * *